United States Patent
Funakoshi et al.

(10) Patent No.: US 6,919,490 B2
(45) Date of Patent: Jul. 19, 2005

(54) METHOD FOR CONTINUOUS PRODUCTION OF A PERFLUOROALKYL IODIDE TELOMER

(75) Inventors: Yoshio Funakoshi, Settsu (JP); Jun Miki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/473,150

(22) PCT Filed: Apr. 17, 2002

(86) PCT No.: PCT/JP02/03811

§ 371 (c)(1), (2), (4) Date: Oct. 9, 2003

(87) PCT Pub. No.: WO02/085823

PCT Pub. Date: Oct. 31, 2002

(65) Prior Publication Data

US 2004/0116753 A1 Jun. 17, 2004

(30) Foreign Application Priority Data

Apr. 17, 2001 (JP) ........................ 2001-118337

(51) Int. Cl.⁷ .................... C07C 17/04; C07C 17/278; C07C 17/272
(52) U.S. Cl. .................. 570/172; 570/175; 570/171
(58) Field of Search ................. 570/171, 172, 570/175

(56) References Cited

U.S. PATENT DOCUMENTS

| 5,068,471 A | 11/1991 | Paul et al. |
| 5,268,516 A | 12/1993 | Bertocchio et al. |
| 5,639,923 A | 6/1997 | Von Werner |
| 5,650,545 A | 7/1997 | Bertocchio et al. |
| 5,929,292 A | 7/1999 | Shimoyama et al. |

FOREIGN PATENT DOCUMENTS

| CA | 2166024 | * | 6/1996 |
| DE | 1 443 517 | | 10/1968 |
| EP | 718262 A1 | | 6/1996 |
| GB | 1096687 | | 12/1967 |
| GB | 1 535 408 | | 12/1978 |
| JP | 6-340560 | | 12/1994 |

OTHER PUBLICATIONS

Q. Chen et al.; "Copper–Induced Telomerization of Tetrafluoro–ethylene with Fluoroalkyl Iodides"; *Journal of Fluorine Chemistry*; vol. 36; 1987; pp. 483–489./Cited in the International Search Report.

* cited by examiner

Primary Examiner—Elvis O. Price
(74) Attorney, Agent, or Firm—Armstrong, Kratz, Quintos, Hanson & Brooks, LLP

(57) ABSTRACT

The present invention relates to a process for continuously producing a perfluoroalkyl iodide represented by the general formula $R_f(CF_2CF_2)_nI$, wherein $R_f$ is a $C_{1-6}$ perfluoroalkyl and n is an integer from 1 to 4, the method comprising continuously supplying a perfluoroalkyl iodide as a telogen represented by the general formula $R_fI$, wherein $R_f$ is as defined above, and tetrafluoroethylene as a taxogen to a tubular reactor packed with a metal catalyst comprising a powdery spherical metal or a sintered metal; and conducting telomerization at a temperature of 60 to 160° C. under a pressure of 0.1 to 5 MPa (gauge pressure).

According to the present invention, medium-chain perfluoroalkyl iodides can be continuously and efficiently produced with little generation of impurities, such as hydrogen-containing organic compounds and the like.

8 Claims, No Drawings

METHOD FOR CONTINUOUS PRODUCTION OF A PERFLUOROALKYL IODIDE TELOMER

TECHNICAL FIELD

The present invention relates to a continuous production process for perfluoroalkyl iodide telomers.

BACKGROUND OF THE INVENTION

Perfluoroalkyl iodides having about 6 to 12 carbon atoms are useful as ingredients for surfactants and for water- and oil-repellents for fibers.

For the production of perfluoroalkyl iodides, industrially employed are processes using telomerization as shown in the following reaction formula:

$$R_fI + nCF_2=CF_2 \rightarrow R_f(CF_2CF_2)_nI$$

wherein $R_f$ is a perfluoroalkyl having 1 to 6 carbon atoms and n is an integer from 1 to 4.

This reaction is known to proceed with heating. German Patent Publication No. 1,443,517, for example, discloses a method wherein a reaction is conducted at a temperature of 250 to 800° C. under a pressure of 2 mmHg to 5 atmospheres with a residence time of 1 hour or less. Such a thermal reaction, however, poses a problem with the production of large amounts of perfluoroalkanes, which are the dimerized products of the perfluoroalkyl radicals generated in the reaction.

Japanese Unexamined Patent Publication No. 305995/1994 discloses a method of thermal telomerization at a high temperature of about 300 to 360° C. In this method, generated are by-products such as iodine and perfluoroalkanes produced by the reactions among the telomers. Especially due to the generation of iodine, reactor corrosion, clogging of pipes and similar components, and other problems are likely to occur. Furthermore, the introduction of tetrafluoroethylene as a taxogen at high temperatures poses a safety problem.

Meanwhile, a variety of catalysts have been developed to conduct telomerization at lower temperatures.

For example, UK Patent No. 1,535,408, U.S. Pat. No. 5,068,471, etc., disclose processes of telomerization through the use of free-radical generators. In these processes, however, perfluoroalkyl radicals react with the free-radical generators and produce, as by-products, hydrogen-containing organic compounds represented by $R_fH$, wherein $R_f$ is a $C_{1-6}$ perfluoroalkyl.

To avoid the generation of undesired long-chain telomers (compounds represented by the formula $R_f(CF_2CF_2)_nI$, where n is 5 or more), the concentration of starting telogens ($R_fI$) is generally increased and the concentration of taxogens is decreased. As a result, the conversion to the desired medium-chain telomers (compounds represented by the formula $R_f(CF_2CF_2)_nI$, where n is 1 to 4) is low, and the starting telogens ($R_fI$) are recycled by distillation.

However, it is difficult to separate the by-product (i.e., $R_fH$) from the starting compound (i.e., $R_fI$). Thus, when telomerization is continuously carried out, $R_fH$ causes a disadvantage of decreasing reaction efficiency due to its accumulation in the telogen.

Chen, et al., (Preliminary Note, *Journal of Fluorine Chemistry* 36 (1987), pp. 483–489) disclose the use of copper powder as a catalyst for telomerization. This reaction proceeds at a low temperature of 80 to 100° C., and moreover, is advantageous for achieving a reaction time that is shorter than that of telomerization conducted at high temperatures.

Japanese Unexamined Patent Publication No. 239335/1996 describes zinc, magnesium, vanadium, rhenium, rhodium, ruthenium, platinum and silver as telomerization catalysts. Moreover, Japanese Unexamined Patent Publication No. 239336/1996 and other publications disclose, in copper-catalyzed telomerization, a method employing other transition metal as a co-catalyst.

However, even when the aforementioned various catalysts are used, their catalytic activities are still insufficient, and the selectivity for medium-chain telomeric compounds, in which n is 4 or smaller, is also unsatisfactory.

DISCLOSURE OF THE INVENTION

A primary object of the present invention is to provide a process for producing medium-chain perfluoroalkyl iodides through telomerization, said process being an industrially advantageous process enabling the continuous and efficient production of medium-chain perfluoroalkyl iodides at low temperatures and generating few impurities, such as hydrogen-containing organic compounds and the like.

The inventors conducted extensive research to achieve the above objective and found as a result that medium-chain telomers can be continuously and efficiently produced in a short period of time at a relatively low temperature with little impurity generation according to a telomerization method wherein a telogen and a taxogen used as starting compounds are supplied to a tubular reactor packed with a metal catalyst comprising a powdery spherical metal or a sintered metal. The present invention has been accomplished based on the finding.

In particular, the present invention provides a continuous production process for perfluoroalkyl iodides as described below:

1. A process for continuously producing a perfluoroalkyl iodide represented by the general formula $$R_f(CF_2CF_2)_nI$$

wherein $R_f$ is a $C_{1-6}$ perfluoroalkyl and n is an integer from 1 to 4,
the method comprising:
   continuously supplying a perfluoroalkyl iodide as a telogen represented by the general formula $$R_fI$$

wherein $R_f$ is as defined above, and tetrafluoroethylene as a taxogen to a tubular reactor packed with a metal catalyst comprising a powdery spherical metal or a sintered metal; and
   conducting telomerization at a temperature of 60 to 160° C. under a pressure of 0.1 to 5 MPa (gauge pressure).

2. A process according to Item 1, wherein the metal catalyst is a powdery spherical metal having an average particle diameter of 1 to 200 μm.

3. A process according to Item 1, wherein the metal catalyst is a sintered metal composed of metal component having an average particle diameter of 50 μm to 0.5 mm.

4. A process according to Item 1, wherein the reaction space of the tubular reactor has a length/diameter ratio of 5 to 1,000.

5. A process according to Item 1, wherein a solution is continuously supplied to the reactor to conduct telomerization, said solution being obtained by dissolving tetrafluoroethylene as a taxogen in the perfluoroalkyl iodide as a telogen.

6. A process according to Item 1, wherein the metal catalyst is a powdery spherical metal or a sintered metal, the catalyst comprising copper metal, tin metal, or tin metal mixed with copper as a co-catalyst.

The production process of the invention is a process to produce a perfluoroalkyl iodide represented by the general formula $R_f(CF_2CF_2)_nI$, wherein $R_f$ is a $C_{1-6}$ perfluoroalkyl and n is an integer from 1 to 4, by subjecting a perfluoroalkyl iodide as a telogen represented by the general formula $R_fI$, wherein $R_f$ is as defined above, to reaction with tetrafluoroethylene as a taxogen.

In the process of the invention, a tubular reactor packed with a metal catalyst comprising a powdery spherical metal or a sintered metal is used as a reactor. Telomerization is conducted by continuously supplying to this reactor a perfluoroalkyl iodide as a telogen represented by the general formula $R_fI$, wherein $R_f$ is as defined above, and tetrafluoroethylene as a taxogen.

Tubular reactors usable herein include those having a cylindrical, elongated reaction space, preferably those with a length/inner diameter ratio of about 5 to about 1,000, and more preferably those with a length/inner diameter ratio of about 10 to about 200. The cross-sectional area of the reaction space of the tubular reactor may generally have, although not limited to, a free passage cross-section of about 1 to about 100 $cm^2$. An excessively large diameter of a tubular reactor is not preferable because reaction heat accumulates in the reactor, thereby making control of telomerization difficult. An excessive rate in supplying the starting compounds is not preferable because the amount of unreacted taxogens is likely to increase. Examples of materials for the tubular reactor include, although are not limited to, stainless steel, copper, Hastelloy, glass lining, etc.

A powdery spherical metal or a sintered metal is used as a catalyst to be packed into the tubular reactor. When the powdery spherical metal is used, the average particle diameter thereof is preferably about 1 to about 200 $\mu$m, and more preferably about 10 to about 45 $\mu$m. Such a powdery spherical metal has, for example, an apparent density of about 4.6 to about 5.5 $g/cm^3$ and thus is a high-density catalyst of low porosity. In the sintered metal, the average particle diameter of the metal particles used for the sintered metal is preferably from about 1 $\mu$m to about 0.5 mm, and more preferably about 100 $\mu$m to about 0.1 mm. Although the shape of the sintered metal is not limited, an excessively large sintered body results in decrease in metal amount to be packed into a reactor. Usually, the sintered metal may have a rod-like form having a diameter of about 1 to about 20 mm and a length of about 1 to about 100 mm. The sintered metal is, as with the powdery spherical metal, a highly-dense, hardly-deformable catalyst.

As opposed to the powdery spherical metal and sintered metal in the above-described forms, metal catalysts in the form of, for example, flakes, electrolytic powder or the like have a low apparent density and are porous. The use of these catalysts is not preferable because the catalysts may be compressed during telomerization, thereby generating high pressure in the intake port of the tubular reactor and tending to hinder the supply of the starting materials.

Types of metal catalysts are not limited insofar as they practically exhibit catalytic action to the aforementioned telomerization. Examples of such metals usable herein are copper, tin, zinc, magnesium, vanadium, rhenium, rhodium, ruthenium, platinum, silver, alloys of these metals, mixtures of these metals, etc. Further, alloys made of any of these metals with small amounts of other transition metal can also be used. Transition metals usable herein include metals that exhibit by themselves no catalytic action or very small catalytic action, such as iron, nickel, chromium, molybdenum, tungsten, titanium, etc.

In particular, when copper, tin, or tin mixed with copper as a co-catalyst is used as a catalyst, catalytic activity and selectivity for medium-chain telomers are improved. In addition, the use of tin mixed with copper as a co-catalyst costs less than the use of copper alone. Further, a copper-tin alloy has a melting point lower than that of copper, providing an advantage of easier production of sintered bodies. A mixture of tin powder and copper powder, tin-copper alloy, and the like are usable as the tin mixed with copper as a co-catalyst. Both tin and copper can be used as a catalyst for telomerization, and therefore the proportion thereof can be selected at will. Also usable are, for example, commercially available bronze powder, which has excellent moldability, sintering properties, strength and other properties, and an alloy having a copper proportion of 90 mass % and a tin proportion of 10 mass %.

In the production process of the invention, for example, tetrafluoroethylene as a taxogen is dissolved in a perfluoroalkyl iodide as a telogen, and the resulting solution is supplied to the reactor through an intake port to bring the solution in contact with the metal catalyst packed into the reactor, thereby enabling telomerization to proceed continuously. This reaction is a liquid-solid two-phase reaction. The telomer generated by telomerization is in the liquid state in the reactor, and it can be separated from the metal catalyst through liquid-solid separation using a filter or other means adjacent to the exit port of the tubular reactor, and discharged from the reactor.

Telogens to be used as starting compounds are represented by the above-described general formula $R_fI$. Specific examples thereof are 2-iodoperfluoropropane, 1-iodoperfluoroethane, 1-iodoperfluorobutane, 1-iodoperfluorohexane, etc. These telogens can be used alone or in combination of two or more species.

Among these telogens, when 1-iodoperfluorobutane or 1-iodoperfluorohexane is used, reaction speed is increased 1.4 times or 3.0 times, compared with the reaction speed obtained by the use of 1-iodoperfluoroethane. Therefore, these lower telogens may be used alone or in combination in the present invention.

The reaction temperature is preferably in a range of about 60 to about 160° C. and more preferably about 100 to about 140° C. Excessively low reaction temperatures are not preferable due to insufficient reaction speed. On the other hand, when reaction temperatures exceed the range described above, although telomerization progresses, they increase a cost and a risk to safety.

The pressure during the reaction is preferably in a range of about 0.1 to about 5 MPa (gauge pressure). Although the reaction progresses under a pressure that is below the range specified above, it is not preferable due to decreased space-time yields. On the other hand, when the reaction pressure exceeds the aforementioned range, although telomerization progresses, it increases a cost and a risk to safety.

In the production process of the invention, the rate of feeding the telogen and taxogen, the rate of discharging the reaction solution, the amount of catalysts used, etc., can be readily selected by conducting preliminary experiments.

Although the ratio of telogen to taxogen, contact time, etc., can not be generalized because they depend on the types of starting compounds, mixing ratio, reaction time and so on, preferable results can be obtained from a tetrafluoroethylene concentration (tetrafluoroethylene/(tetrafluoroethylene+telogen)) of about 1 to about 15 mol % and a catalyst contact time of about 10 seconds to about 9 minutes.

In the production process of the invention, complicated operations for recycling metal catalysts are not required, and generation of long-chain telomers is inhibited by controlling the amount of telogen and taxogen to be supplied, thereby easily enabling an increase in selectivity for the desired medium-chain telomers (n=1 to 5). Moreover, as the reaction solution discharged from the reactor does not contain metal catalysts, the desired product can therefore be readily isolated therefrom by distillation or like procedure without separation/recovery of the metal catalysts.

As described above, according to the production process of the invention, the desired product, i.e., medium-chain telomers, can be continuously and efficiently produced at relatively low temperatures. Thus, it is an industrially advantageous process in producing medium-chain telomers.

BEST MODE FOR CARRYING OUT THE INVENTION

Examples are given below to describe the invention in more detail.

EXAMPLE 1

A stainless-steel tube with an external diameter of ⅜ inches that was packed with 46 g of spherical copper powder (produced by Mitsui Mining & Smelting Co., Ltd., particle size: 330 mesh or less, average particle diameter: 19 μm) was used as a tubular reactor. A starting solution wherein tetrafluoroethylene (TFE) was dissolved in a perfluoroethyl iodide (TFE concentration: TFE/(telogen+TFE)=4.25 mol %) was continuously supplied to the stainless-steel tube to conduct telomerization under a reaction pressure of 3 MPa (gauge pressure) at a starting solution supply rate of 9.0 ml/min. The reaction was conducted at a temperature ranging from 60 to 120° C.

The reaction solution discharged from the stainless-steel tube was cooled and analyzed by gas chromatography for its components. Results are shown in Table 1.

TABLE 1

| Reaction temperature (° C.) | Component distribution in product (mol %) n Value $(C_2F_5(CF_2CF_2)_nI)$ | | | | | | TFE conversion (%) |
|---|---|---|---|---|---|---|---|
| | 0 | 1 | 2 | 3 | 4 | More than 4 | |
| 60 | 99.66 | 0.25 | 0.056 | 0.0163 | 0.0068 | 0.0109 | 17.59 |
| 80 | 99.7 | 0.25 | 0.029 | 0.0091 | 0.0036 | 0.0083 | 21.59 |
| 100 | 99.56 | 0.37 | 0.049 | 0.012 | 0.0041 | 0.0049 | 28.36 |
| 120 | 99.34 | 0.55 | 0.084 | 0.020 | 0.0047 | 0.0213 | 47.55 |
| 140 | 98.87 | 0.94 | 0.15 | 0.029 | 0.0054 | 0.0056 | 59.7 |

EXAMPLE 2

A stainless-steel tube with an external diameter of ⅜ inches that was packed with 46 g of spherical copper powder (produced by Mitsui Mining & Smelting Co., Ltd., particle size: 330 mesh or less, average particle diameter: 19 μm) was used as a tubular reactor. A starting solution wherein tetrafluoroethylene (TFE) was dissolved in a perfluoroethyl iodide (TFE concentration: 4.25 mol %) was continuously supplied to the stainless-steel tube to conduct telomerization under a reaction pressure of 3 MPa (gauge pressure) at a reaction temperature of 120° C. in a reaction volume of 4 ml. The starting solution was supplied at a rate of 1.4 ml/min, 4.4 ml/min or 9 ml/min.

The reaction solution discharged from the stainless-steel tube was cooled and analyzed by gas chromatography for its components. Results are shown in Table 2.

TABLE 2

| Rate of supplying the starting solution (ml/min) | Component distribution in product (mol %) n Value $(C_2F_5(CF_2CF_2)_nI)$ | | | | | | TFE conversion (%) |
|---|---|---|---|---|---|---|---|
| | 0 | 1 | 2 | 3 | 4 | More than 4 | |
| 1.4 | 83.11 | 14.89 | 1.66 | 0.27 | 0.059 | 0.011 | 99.89 |
| 4.4 | 84.32 | 13.34 | 1.84 | 0.39 | 0.087 | 0.413 | 80.14 |
| 9.0 | 99.34 | 0.55 | 0.084 | 0.020 | 0.0047 | 0.0213 | 47.55 |

EXAMPLE 3

A stainless-steel tube with an external diameter of ⅜ inches that was packed with 18 g of spherical copper powder (produced by Mitsui Mining & Smelting Co., Ltd., particle size: 330 mesh or less, average particle diameter: 19 μm) was used as a tubular reactor. A starting solution wherein tetrafluoroethylene (TFE) was dissolved in perfluoroethyl iodide was continuously supplied to the stainless-steel tube to conduct telomerization under a reaction pressure of 4.5 MPa (gauge pressure) at a starting solution supply rate of 4.4 ml/min and a reaction temperature of 120° C. The concentration of tetrafluoroethylene (TFE) in the starting solution was 3.03 mol %, 7.06 mol %, 8.42 mol % or 11.35 mol %.

The reaction solution discharged from the stainless-steel tube was cooled and analyzed by gas chromatography for its components. Results are shown in Table 3.

TABLE 3

| TFE concentration (mol %) | Component distribution in product (mol %) n value $(C_2F_5(CF_2CF_2)_nI)$ | | | | | | TFE conversion (%) |
|---|---|---|---|---|---|---|---|
| | 0 | 1 | 2 | 3 | 4 | More than 4 | |
| 3.03 | 99.71 | 0.27 | 0.028 | 0.002 | — | — | 10.54 |
| 7.06 | 98.32 | 1.29 | 0.3 | 0.07 | 0.02 | — | 28.68 |
| 8.42 | 97.74 | 1.65 | 0.44 | 0.12 | 0.03 | 0.02 | 33.37 |
| 11.35 | 96.47 | 2.37 | 0.75 | 0.26 | 0.09 | 0.06 | 41.25 |

EXAMPLE 4

A stainless-steel tube with an external diameter of ⅜ inches that was packed with 18 g of spherical copper powder (produced by Mitsui Mining & Smelting Co., Ltd., particle size: 330 mesh or less, average particle diameter: 19 μm) was used as a tubular reactor. A starting solution wherein tetrafluoroethylene (TFE) as a taxogen was dissolved in a telogen, i.e., perfluoroethyl iodide, perfluorobutyl iodide or perfluorohexyl iodide (TFE concentration: 3.14 mol %) was continuously supplied to the stainless-steel tube to conduct telomerization under a reaction pressure of 4.5 MPa (gauge pressure) at a starting solution supply rate of 8.3 ml/min and a reaction temperature of 120° C.

The reaction solution discharged from the stainless-steel tube was cooled and analyzed by gas chromatography for its components. Results are shown in Table 4.

TABLE 4

| n Value of starting telomer[*1] | Component distribution in product (mol %) n Value $(C_2F_5(CF_2CF_2)_nI)$ | | | | | | Rate of TFE disappearance[*2] |
|---|---|---|---|---|---|---|---|
| | 0 | 1 | 2 | 3 | 4 | 5 | |
| 0 | 99.62 | 0.34 | 0.042 | 0.0046 | — | — | 0.000665 |
| 1 | — | 99.62 | 0.35 | 0.029 | — | — | 0.000922 |
| 2 | — | — | 98.71 | 1.16 | 0.11 | 0.013 | 0.00194 |

[*1]the value of n in the formula: $C_2F_5(CF_2CF_2)_nI$
[*2]the rate of TFE disappearance per mole of the starting telomer (sec$^{-1}$mol$^{-1}$)

EXAMPLE 5

As a metal catalyst, 63.9 g of spherical copper powder (produced by Fukuda Metal Foil Powder Co., Ltd., average particle diameter: 100 μm), 59.4 g of spherical copper-tin alloy (copper: 90 mass %, tin: 10 mass %) (produced by Fukuda Metal Foil Powder Co., Ltd., average particle diameter: 200 μm) or 28.4 g of spherical tin powder (produced by Kishida Chemical Co., Ltd., average particle diameter: 75 μm) was used and packed into a stainless-steel tube with an external diameter of ⅜ inches.

A solution wherein tetrafluoroethylene (TFE) was dissolved in perfluoroethyl iodide (TFE concentration: 9.4 mol %) was used as a starting solution, and continuously supplied to the stainless-steel tube to conduct telomerization under a reaction pressure of 3.0 MPa (gauge pressure) at a starting solution supply rate of 2.0 ml/min and a reaction temperature of 120° C.

The reaction solution discharged from the stainless-steel tube was cooled and analyzed by gas chromatography for its components. The surface area of the metal catalysts was measured by a surface area analyzer (Yuasa-Ionics Co., Ltd.)

Table 5 shows the results.

TABLE 5

| Catalyst | | | TFE conversion (%) | TFE decrease rate (mol/s) | TFE decrease rate per m² of catalyst surface area (mol/s · m²) |
|---|---|---|---|---|---|
| Type | Amount used (g) | Surface area (m²/g) | | | |
| Copper-tin alloy | 59.44 | 0.012 | 24.5 | 0.0028 | 3.93E−03 |
| Copper powder | 63.88 | 0.044 | 40.6 | 0.006 | 2.13E−03 |
| Tin powder | 28.36 | 0.191 | 93.5 | 0.0132 | 2.44E−03 |

EXAMPLE 6

A stainless-steel tube with an external diameter of ⅜ inches that was packed with 118 g of a sintered metal (diameter: 1 mm, length: 10 mm) of spherical copper powder was used as a tubular reactor. A starting solution wherein tetrafluoroethylene (TFE) was dissolved in perfluoroethyl iodide (TFE concentration: 10 mol %) was continuously supplied to the stainless-steel tube to conduct telomerization under a reaction pressure of 4.5 MPa (gauge pressure) at a reaction temperature of 120° C. and a starting solution supply rate of 2 ml/min, 3 ml/min or 5 ml/min.

The reaction solution discharged from the stainless-steel tube was cooled and analyzed by gas chromatography for its components. The results are shown in Table 6.

TABLE 6

| Rate of supplying the starting solution (ml/min) | Component distribution in product (mol %) n Value $(C_2F_5(CF_2CF_2)_nI)$ | | | | | | TFE conversion (%) |
|---|---|---|---|---|---|---|---|
| | 0 | 1 | 2 | 3 | 4 | More than 4 | |
| 2 | 97.65 | 1.62 | 0.48 | 0.16 | 0.04 | 0.04 | 60.4 |
| 3 | 98.55 | 1 | 0.3 | 0.1 | 0.03 | 0.02 | 28.9 |
| 5 | 99.93 | 0.49 | 0.14 | 0.04 | — | — | 1.45 |

EXAMPLE 7

A stainless-steel tube with an external diameter of ⅜ inches that was packed with 184 g of spherical copper powder (produced by Mitsui Mining & Smelting Co., Ltd., particle size: 330 mesh or less, average particle diameter: 19 μm) was used as a tubular reactor. A starting solution wherein tetrafluoroethylene (TFE) was dissolved in perfluoroethyl iodide (TFE concentration: 10 mol %) was continuously supplied to the stainless-steel tube to conduct telomerization under a reaction pressure of 4.5 MPa (gauge pressure) at a reaction temperature of 120° C. and a starting solution supply rate of 4.2 ml/min.

The reaction solution discharged from the stainless-steel tube was cooled and analyzed by gas chromatography for its components. Results are shown in Table 7.

COMPARATIVE EXAMPLE 1

Into a stainless-steel, 230-ml pressurized mixing vessel reactor equipped with a stirrer, 400 g of 1-iodoperfluoroethane and 184 g of spherical copper powder (produced by Mitsui Mining & Smelting Co., Ltd., particle size: 330 mesh or less, average particle diameter: 19 μm) were charged. A starting solution wherein tetrafluoroethylene (TFE) was dissolved in perfluoroethyl iodide (TFE concentration: 10 mol %) was supplied to the reactor to continuously conduct telomerization under a reaction pressure of 1.9 MPa (gauge pressure) at a reaction temperature of 120° C. and a starting solution supply rate of 2.3 ml/min.

The reaction solution thus obtained was cooled and analyzed by gas chromatography for its components. Results are shown in Table 7.

TABLE 7

| | Reactor | TFE (mol %) | Reaction time (min) | Component distribution in product (mol %) n Value $(C_2F_5(CF_2CF_2)_nI)$ | | | | | | TFE conversion (%) |
|---|---|---|---|---|---|---|---|---|---|---|
| | | | | 0 | 1 | 2 | 3 | 4 | 5 | |
| Ex. 7 | Tubular | 10 | 8.3 | 93.15 | 5.5 | 0.97 | 0.26 | 0.069 | 0.048 | 93.8 |
| Comp Ex. 1 | Vessel | 10.3 | 100 | 94.13 | 4.49 | 1.03 | 0.26 | 0.06 | 0.03 | 92.3 |

What is claimed is:

1. A process for continuously producing a perfluoroalkyl iodide represented by the general formula $$R_f(CF_2CF_2)_nI$$

wherein $R_f$ is a $C_{1-6}$ perfluoroalkyl and n is an integer from 1 to 4, the method comprising:
   continuously supplying a perfluoroalkyl iodide as a telogen represented by the general formula $$R_fI$$

wherein $R_f$ is as defined above, together with tetrafluoroethylene as a taxogen, to a tubular reactor packed with a metal catalyst comprising a powdery spherical metal or a sintered metal; and
   continuously conducting telomerization at a temperature of 60 to 160° C. under a pressure of 0.1 to 5 MPa (gauge pressure).

2. A process according to claim 1, wherein the metal catalyst is a powdery spherical metal having an average particle diameter of 1 to 200 μm.

3. A process according to claim 1, wherein the metal catalyst is a sintered metal composed of metal component having an average particle diameter of 50 μm to 0.5 mm.

4. A process according to claim 1, wherein the reaction space of the tubular reactor has a length/diameter ratio of 5 to 1,000.

5. A process according to claim 1, wherein a solution is continuously supplied to the reactor to conduct telomerization, said solution being obtained by dissolving tetrafluoroethylene as a taxogen in the perfluoroalkyl iodide as a telogen.

6. A process according to claim 1, wherein the metal catalyst is a powdery spherical metal or a sintered metal, the catalyst comprising copper metal, tin metal, or tin metal mixed with copper as a co-catalyst.

7. The process according to claim 1, further comprising:
   continuously discharging a reaction solution from said tubular reactor.

8. The process according to claim 7, further comprising:
   recovering said perfluoroalkyl iodide from said reaction solution.

* * * * *